(12) United States Patent
Krause et al.

(10) Patent No.: US 12,419,666 B2
(45) Date of Patent: Sep. 23, 2025

(54) PROBES FOR SURGICAL ACCESS SYSTEM

(71) Applicant: Stryker European Operations Limited, Carrigtwohill (IE)

(72) Inventors: Steven F. Krause, Oakland, NJ (US); Spencer Popejoy, Ringwood, NJ (US); Heesang Samuel Lee, Montvale, NJ (US); Douglas G. Pedrick, Newburgh, NY (US); Nathaniel G. Magee, Hoboken, NJ (US)

(73) Assignee: Stryker European Operations Limited, Carrigtwohill (IE)

( * ) Notice: Subject to any disclaimer, the term of this patent is extended or adjusted under 35 U.S.C. 154(b) by 0 days.

(21) Appl. No.: 18/459,760

(22) Filed: Sep. 1, 2023

(65) Prior Publication Data

US 2023/0404622 A1    Dec. 21, 2023

Related U.S. Application Data (63) Continuation of application No. 16/681,069, filed on Nov. 12, 2019, now Pat. No. 11,771,464.
(Continued)

(51) Int. Cl.
  *A61B 17/34* (2006.01)
  *A61B 5/24* (2021.01)
  *A61B 17/00* (2006.01)

(52) U.S. Cl.
  CPC ...... *A61B 17/3496* (2013.01); *A61B 17/3423* (2013.01); *A61B 5/24* (2021.01); *A61B 2017/00039* (2013.01); *A61B 2017/00106* (2013.01); *A61B 2017/00115* (2013.01); *A61B 2017/0042* (2013.01); *A61B 2017/00858* (2013.01)

(58) Field of Classification Search
  CPC ... A61B 17/3496; A61B 17/3423; A61B 5/24; A61B 2017/00039; A61B 2017/00106; A61B 2017/00115; A61B 2017/0042; A61B 2017/00858
  See application file for complete search history.

(56) References Cited

U.S. PATENT DOCUMENTS

| 6,466,817 B1 | 10/2002 | Kaula et al. |
| 6,564,078 B1 | 5/2003 | Marino et al. |

(Continued)

FOREIGN PATENT DOCUMENTS

| WO | 2018039228 A1 | 3/2018 | |
| WO | WO-2018097987 A1 * | 5/2018 | ....... A61B 17/22012 |

*Primary Examiner* — Ashley L Fishback
(74) *Attorney, Agent, or Firm* — Duane Morris LLP (57) ABSTRACT

In one embodiment, the present disclosure relates to a probe for use in minimally invasive surgery. The probe includes a shaft and a tip extending from the shaft. The tip includes a bulbous shape with a smooth and rounded outer surface. In some embodiments, the shaft is separated from the tip by a neck such that both the shaft and the tip expand outward from a concave surface of the neck. In some embodiments, one or both of a neuromonitoring element and an ultrasound sensor are disposed on the tip. In some embodiments, a probe may include a surface feature that resists expulsion of the probe from a human body when the probe is disposed in the human body. In further embodiments, a probe may include insulated material over a first surface region and conductive material over a second surface region.

7 Claims, 12 Drawing Sheets

Related U.S. Application Data

(60) Provisional application No. 62/760,429, filed on Nov. 13, 2018.

(56) References Cited

U.S. PATENT DOCUMENTS

| | | |
|---|---|---|
| 6,760,616 B2 | 7/2004 | Hoey et al. |
| 7,207,949 B2 | 4/2007 | Miles et al. |
| 7,522,953 B2 | 4/2009 | Kaula et al. |
| 7,582,058 B1 | 9/2009 | Miles et al. |
| 7,691,057 B2 | 4/2010 | Miles et al. |
| 7,819,801 B2 | 10/2010 | Miles et al. |
| 7,905,840 B2 | 3/2011 | Pimenta et al. |
| 7,918,891 B1 | 4/2011 | Curran et al. |
| 8,050,769 B2 | 11/2011 | Gharib et al. |
| D652,519 S | 1/2012 | Miles et al. |
| D652,921 S | 1/2012 | Miles et al. |
| D652,922 S | 1/2012 | Miles et al. |
| 8,137,284 B2 | 3/2012 | Miles et al. |
| D666,292 S | 8/2012 | Miles et al. |
| D666,293 S | 8/2012 | Miles et al. |
| D666,294 S | 8/2012 | Miles et al. |
| 9,655,646 B2 | 5/2017 | Richey |
| 11,331,114 B2 | 5/2022 | Deepa |
| 2009/0005675 A1 | 1/2009 | Grunwald et al. |
| 2014/0343348 A1 | 11/2014 | Kaplan et al. |
| 2019/0298328 A1 | 10/2019 | Popejoy et al. |

* cited by examiner

PROBES FOR SURGICAL ACCESS SYSTEM

CROSS-REFERENCE TO RELATED APPLICATIONS

This application is a continuation of U.S. patent application Ser. No. 16/681,069, filed Nov. 12, 2019, which claims the benefit of the filing date of U.S. Provisional Patent Application No. 62/760,429, filed Nov. 13, 2018, the disclosures of which are hereby incorporated by reference herein in their entireties.

BACKGROUND OF THE INVENTION

In many surgeries, surgical probes are used as part of a procedure to detect the presence of nerves prior to the insertion of surgical instrumentation through an intended surgical path. For instance, probes with neuromonitoring capabilities are an integral part of certain spinal fusion surgeries, including those that require placement of implants and instruments through innervated-muscles (i.e., the psoas muscle). However, many existing probes are subject to reaction forces from the muscle which tend to push out instrumentation from its intended docking point (pull out forces) and otherwise may not have surface features amenable to smooth passage through muscle. Accordingly, there is a need for improved surgical probe structures.

BRIEF SUMMARY OF THE INVENTION

In one embodiment, the present disclosure relates to a probe that includes a shaft, a tip extending from the shaft, and a neuromonitoring probe disposed on the tip. The tip includes a bulbous shape with a smooth and rounded outer surface.

In another embodiment, a probe for use in the human body includes a handle, a shaft connected with the handle and a tip extending from the shaft. Surface features are included on the tip, the shaft or both the tip and the shaft that resist expulsion of the probe from the body.

In yet another embodiment, a probe includes a linear shaft with a bulbous tip at an insertion end and a handle at a trailing end. At a portion of the shaft immediately adjacent to the bulbous tip, the shaft narrows slightly to define a neck. A neuromonitoring element is disposed on the bulbous tip. In some arrangements, the probe is cannulated. In further arrangements, the bulb shaped tip may vary to include different curvatures or a flat shaped front end face.

In another embodiment, a probe includes a bulging shaft that tapers toward a bulb shaped tip at an insertion end of the probe. A neuromonitoring element is disposed on the tip. In some arrangements, part or all of the shaft is triangular in cross section. In still further arrangements, the tip is partially or fully triangular in cross section. Also, sections or full probe body may be multifaceted, not limited to triangular cross section, but many facets (3+) to provide distinct surfaces for neuromonitoring around the surface of the probe body and into the soft tissue/muscle.

In other embodiments, a probe includes a shaft with a length extending from an upper end to a lower end, the upper end having a concave surface and the lower end having a convex surface extending to a rounded tip. A handle is included at an end opposite the rounded tip. At a location on or near the tip is a neuromonitoring element. In another embodiment, a probe includes a shaft that flares outward from a handle and forms a tip at an end opposite the handle, the tip defined by a smooth, convex surface.

In another embodiment, a probe includes a shaft separating a handle and a tip, the shaft having a helical thread formed in its surface. In another embodiment, a probe includes a shaft with a series of repeating protrusions that taper in a direction facing the insertion end. A surface of the protrusions may be angular in some arrangements and curved in other arrangements.

In yet another embodiment, a probe includes a linear shaft with a series of longitudinal grooves spaced around a perimeter of the shaft. The grooves form a rounded cut in a cross section of the probe. In some arrangements, the grooves may have a v-shape or other shape. A tip of the probe is tapered and a terminus of the tip is spaced from an end of the grooves on the shaft.

In yet another embodiment a probe includes a linear shaft separating a handle and a tip. The tip is defined by a smooth, rounded surface that tapers inward from the shaft towards a terminus of the tip such that the largest cross section on the probe is on the shaft.

In yet another embodiment, a probe includes a plurality of longitudinally extending grooves positioned at different locations on a perimeter of the probe. The probe has a tapered tip and a neuromonitoring element disposed on the probe near its distal end. In some arrangements, the grooves on the probe are sized to accommodate disposal of retractor rods therein.

In another embodiment, a probe is made of a clear plastic material and a portion of an exposed surface area on the probe is conductive and connected to a neuromonitoring console. The probe includes a plurality of light emitting devices having at least two different colors. Devices with a particular light color are configured to activate upon detection of electrical activity falling within a unique range.

In another embodiment, a probe includes a single longitudinally extending groove with a neuromontioring element disposed therein. In some examples, the neuromonitoring element snaps into place on a side of the probe. In yet another embodiment, a probe includes a portion comprised of insulating material and another portion comprised of conductive material so that a portion of the conductive material is exposed on the probe surface while the remainder of the probe surface is insulated.

In another embodiment, the probe is a plastic tube sized to fit over a rod of a retractor. A conductive material is disposed on a portion of an external surface of the tube for neuromonitoring.

In one embodiment, a probe for use in minimally invasive surgery includes a shaft and a tip extending from the shaft. The tip includes a bulbous shape with a smooth and rounded outer surface. In some embodiments, the probe may include a neuromonitoring element disposed on the tip. In some embodiments, the shaft may include a proximal portion and a distal portion, the distal portion being between the proximal portion and the tip and having a width narrower than at least one location on each of the proximal portion and the tip. In some embodiments, the proximal portion, the distal portion and the tip may have a continuous smooth surface. In some embodiments, the distal portion of the shaft may include a concave surface. In some embodiments, the tip may have a maximum diameter larger than a maximum diameter of the shaft. In some embodiments, the shaft may have a triangular shape over part of its length. In some embodiments, the probe may include an ultrasound sensor on the tip.

In one embodiment, a probe for use in a human body includes a handle, a shaft portion connected with the handle and a tip portion extending from the shaft portion. At least one of the shaft portion and the tip portion includes a surface feature that resists expulsion of the probe from the human body when the probe is disposed in the human body. In some embodiments, the surface feature may include a plurality of circumferential ridges spaced apart from one another along the shaft portion. In some embodiments, each of the plurality of circumferential ridges may be frusto-conical in shape. In some embodiments, the surface feature may include a plurality of longitudinally extending grooves that are circumferentially spaced apart from one another. In some embodiments, the plurality of longitudinally extending grooves may each have a length with an end proximate to the end surface of the tip portion that is spaced apart from the end surface. In some embodiments, the plurality of longitudinally extending grooves may include a first circumferential spacing between a first groove and second groove of the plurality of longitudinally extending grooves and a second circumferential spacing different from the first circumferential spacing between a third groove and another groove of the plurality of longitudinally extending grooves. In some embodiments, the surface feature may include a helical groove along the shaft portion. In some embodiments, the probe may include an ultrasound sensor on the tip portion.

In one embodiment, a probe for minimally invasive surgery includes a body and a connector. The body has a length including a uniform portion and a tapered convex end portion. The body includes an insulated part and a conductive part, the insulated part covering a first outer surface area of the body and the conductive part covering a second outer surface area of the body at least partially over the tapered end portion of the body. The first outer surface area is greater than the second outer surface area. The connector is electrically connected with the conductive part and is capable of being connected to an external source of electricity so that the conductive part delivers electrical stimulation when the conductive part receives electric current. In some embodiments, the second outer surface area may extend over the length of the body from a first end of the body to a second end of the body opposite the first end. In some embodiments, the body may be a tube with a hollow interior and a closed tip. In some embodiments, the probe may include a first light emitting device adapted to emit a first color when a first range of electrical activity is detected by the probe and a second light emitting device adapted to emit a second color when a second range of electrical activity is detected by the probe. The first color may be different from the second color and the first range may be different from the second range.

BRIEF DESCRIPTION OF THE DRAWINGS

The present disclosure will be better understood on reading the following detailed description of non-limiting embodiments thereof, and on examining the accompanying drawings, in which.

DETAILED DESCRIPTION

Surgical probes are used in many surgeries, including spine surgeries. Certain approaches to the spine, such as the lateral trans-psoas approach, involve the creation of a surgical portal through an opening in the psoas muscle. In such approaches, a probe is used initially to ensure that the passage created does not impinge any nerves. Some examples of how a probe is used as part of this process are described in International Publication No. WO2018/039228 and in U.S. Pat. App. Pub. No. 2019/0298328, both hereby incorporated by reference herein in their entirety. Of course, probes may also be used in many other surgeries where the creation of access may involve a risk of contacting nerves.

Figure 1:
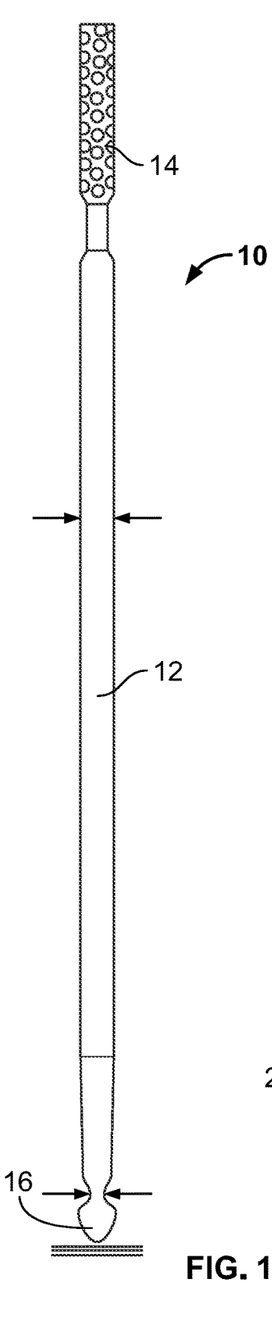
FIG. 1 is a side view of a probe according to one embodiment of the disclosure.
Figure 2:
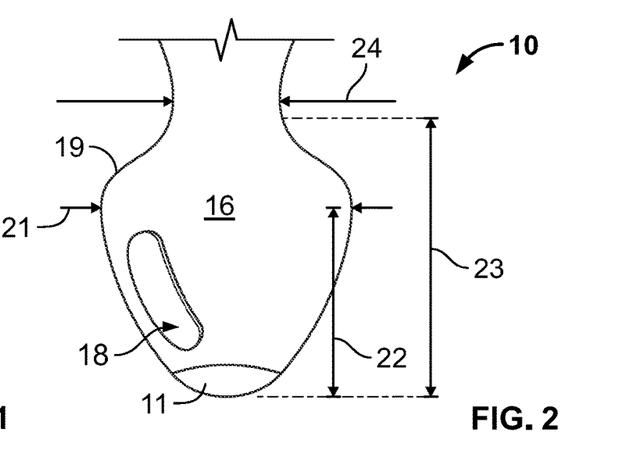
FIG. 2 is a close up view of a tip of the probe of FIG. 1.

FIGS. 1-2 illustrate one embodiment of a probe 10 with, inter alia, a shaft 12, a handle 14 and a tip 16. Tip 16 bulges outward from shaft as shown in FIG. 2 and includes a ledge 19. Ledge 19 preferably acts to block the pull out of probe 10 when the probe is embedded in tissue and provides an alternative placement location for neuromonitoring elements which may be advantageous in certain circumstances. An elongate neuromonitoring element 18 is disposed on a surface of tip 16. In one example, dimensions of the tip include a maximum width 21 of 6 mm, a neck width 24 of 4.5 mm, a length 22 from the maximum width to a terminus 11 of the tip of 6 mm, and a length 23 from the neck to the terminus of 8 mm. Of course, in other examples, the dimensions may vary.

Figure 3:
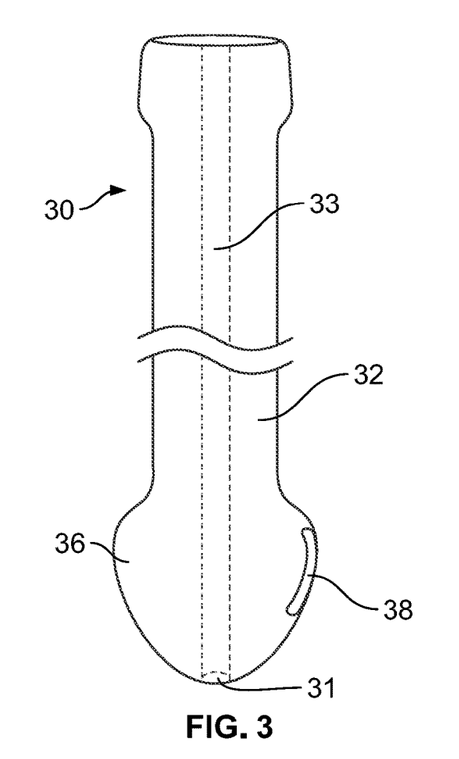
FIG. 3 is a side view of a tip of a probe according to another embodiment of the disclosure.

FIG. 3 illustrates another embodiment of a probe 30 where like reference numerals refer to like elements of probe 10 as illustrated in FIG. 1. Probe 30 includes a ball shaped tip 36 and a cannulation 33. As shown, a neuromonitoring element 38 extends over a majority of a length of the tip. However, such size and position may be varied depending upon the ultimate end use for the probe.

Figures 4, 5, 6:
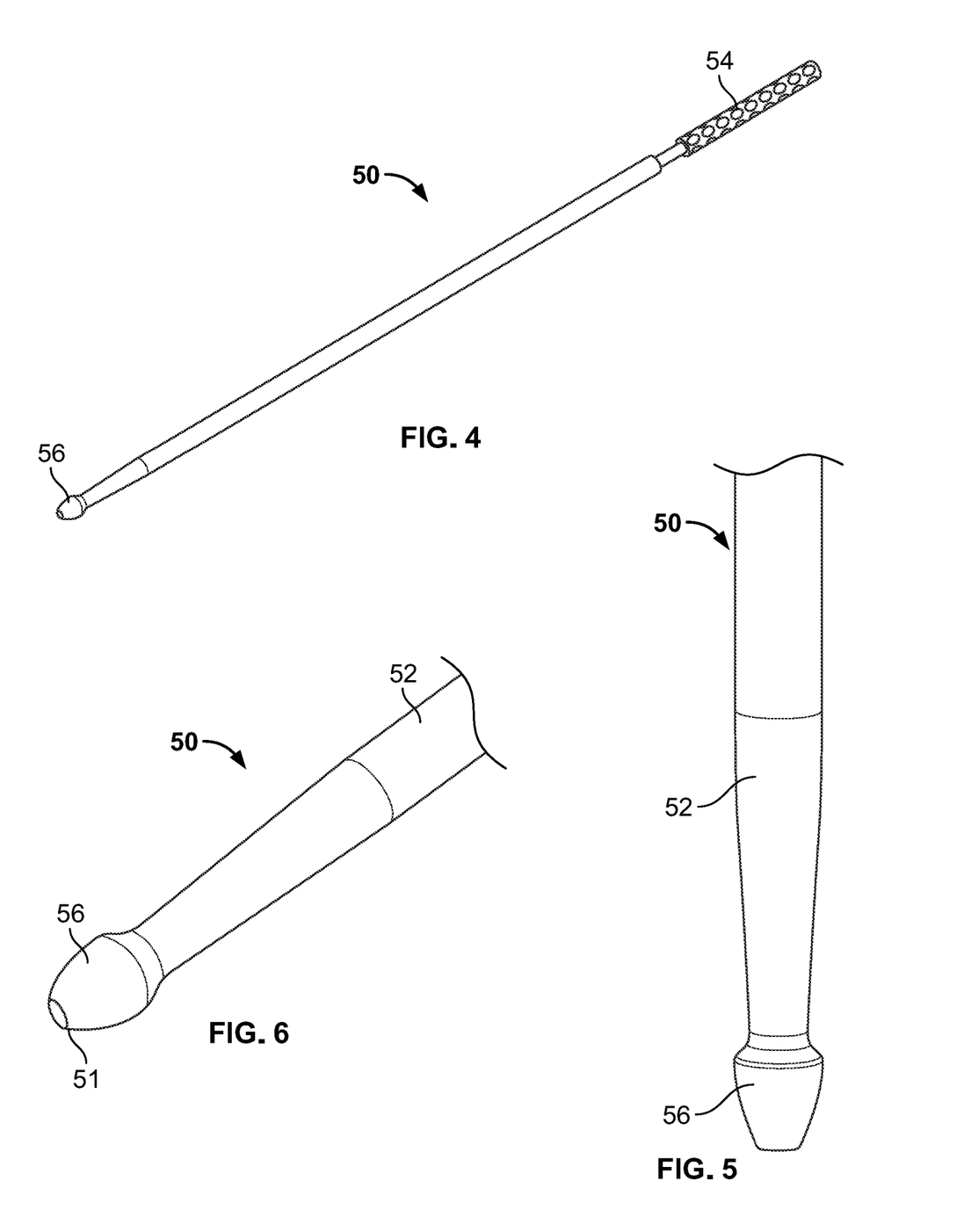
FIG. 4 is a perspective view of a probe according to another embodiment of the disclosure.
FIGS. 5 and 6 are close up views of a distal portion of the probe of FIG. 4.

Yet another embodiment of a probe with a ball shaped tip is illustrated in FIGS. 4-6. Again, like reference numerals refer to like elements of probe 10 as illustrated in FIG. 1. FIGS. 5 and 6 show that tip 56 of probe 50 bulges outward from shaft 52 and then tapers toward a tip with a rounded contour.

Figure 7:
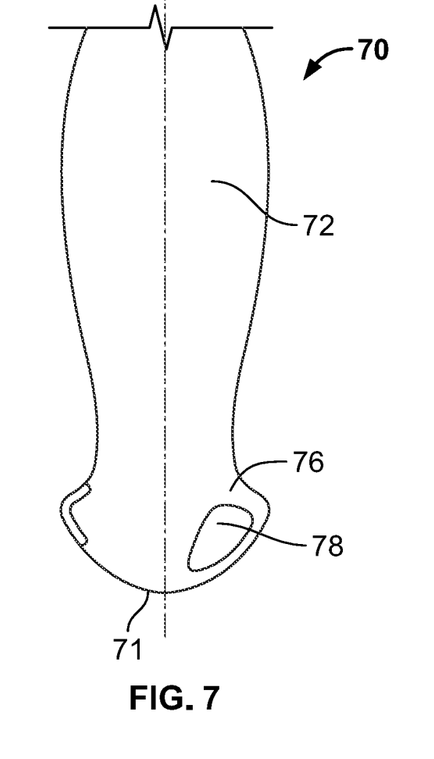
FIG. 7 is a partial side view of a probe according to another embodiment of the disclosure.

FIG. 7 illustrates probe 70 of one embodiment, where like reference numerals refer to like elements of probe 10 as illustrated in FIG. 1. Shaft 72 of probe 70 is bulging toward a central region, forming a convex surface on a surface of the probe in the central region.

Figure 8:
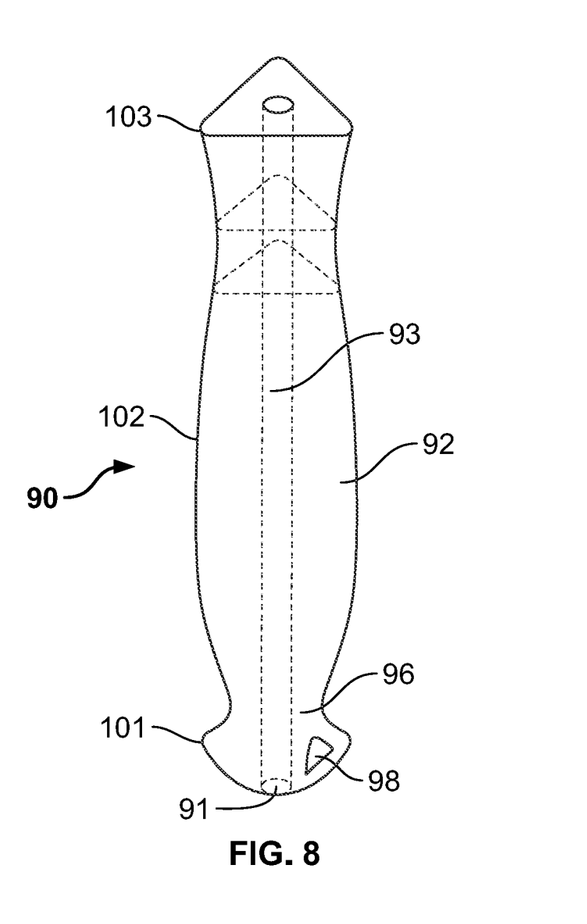
FIG. 8 is a side view of a probe according to another embodiment of the disclosure.

FIG. 8 illustrates probe 90 of yet another embodiment where like reference numerals refer to like elements of probe 10 as illustrated in FIG. 1. Probe 90 is cannulated 93 and includes a widened section at three separate locations 101, 102, 103. Further, probe 90 includes a triangular cross section, as shown at location 103. It is contemplated that the shaft may have a triangular cross section over any portion of its length, ranging from only the extreme end of the shaft to the entirety of the shaft. In some variants, probe 90 may include a nerve hook retaining tissue distal tip.

In each of the embodiments illustrated in FIGS. 1-8, a ledge on the tip of the probe that faces rearward relative to the terminus of the tip, such as ledge 19 in FIG. 2, operates to ensure probe remains in place within muscle tissue once inserted therethrough. In particular, when the probe is embedded within muscle tissue, the tissue creeps over the surface of the probe tip and over the ledge. Thus, forces acting on the probe due to tissue on the front side of the tip that would otherwise cause the probe to withdraw from the muscle are resisted by the ledge pressing against tissue behind it.

Figure 9:
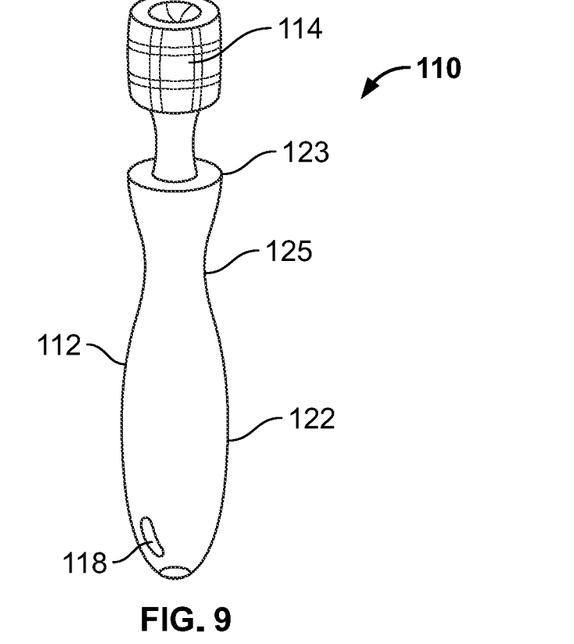
FIG. 9 is a side view of a probe according to another embodiment of the disclosure.
Figure 10:
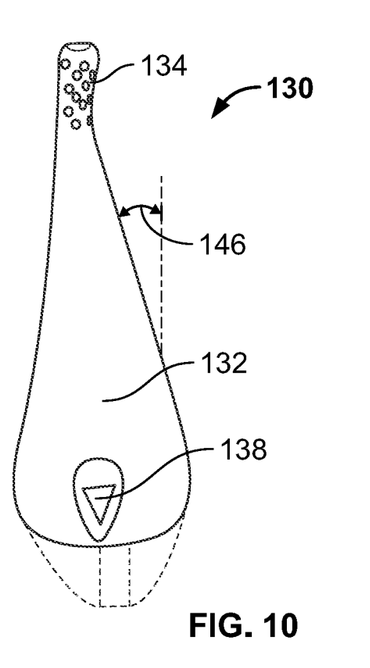
FIG. 10 is a side view of a probe according to another embodiment of the disclosure.
Figure 11:
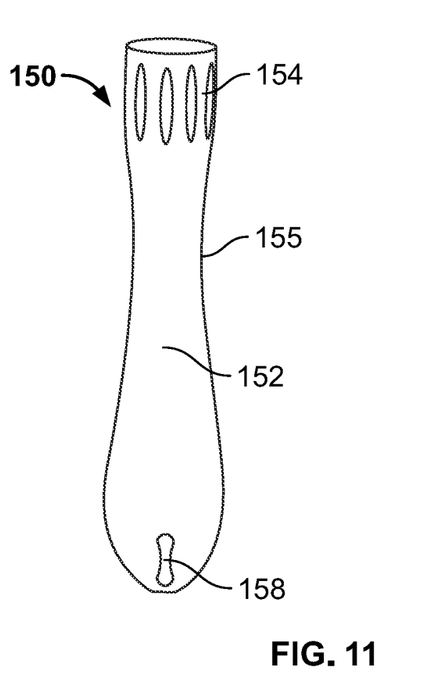
FIG. 11 is a side view of a probe according to another embodiment of the disclosure.

FIGS. 9-11 illustrate probes 110, 130, 150 according to respective embodiments of the disclosure. Like reference numerals of probes 110, 130, 150 in FIGS. 9-11 refer to like elements of probe 10 as illustrated in FIG. 1. Probe 110 shown in FIG. 9 includes a shaft 112 with a rounded surface having a concave region 125 between an upper bulging region 123 and a lower bulging region 122. Lower bulging region 122 includes a convex surface to a tip 111 of probe 110. Probe 130 shown in FIG. 10 includes a handle 134 and a shaft 132, the shaft flaring continuously outward from the handle until rounding to a closed, convex shape at a tip. In this manner, probe 130 is tear drop shaped. Surfaces of probe 130 slope outward between the handle and the tip at an angle 146. In one example, the angle is 0.51 degrees. Further, in some examples, probe 130 may be a composite comprised of multiple materials. One example of such an arrangement is shown in FIG. 10 with the inclusion of the phantom lines on probe 130 to signify the use of two different materials. Probe 150 shown in FIG. 11 includes a concave region 155 separating an upper bulging region with a handle 154 and a lower bulging region with a neuromonitoring element 158. Each of probes 110, 130, 150 includes a complex curvature that may be related to an anatomical shape.

Figure 12:
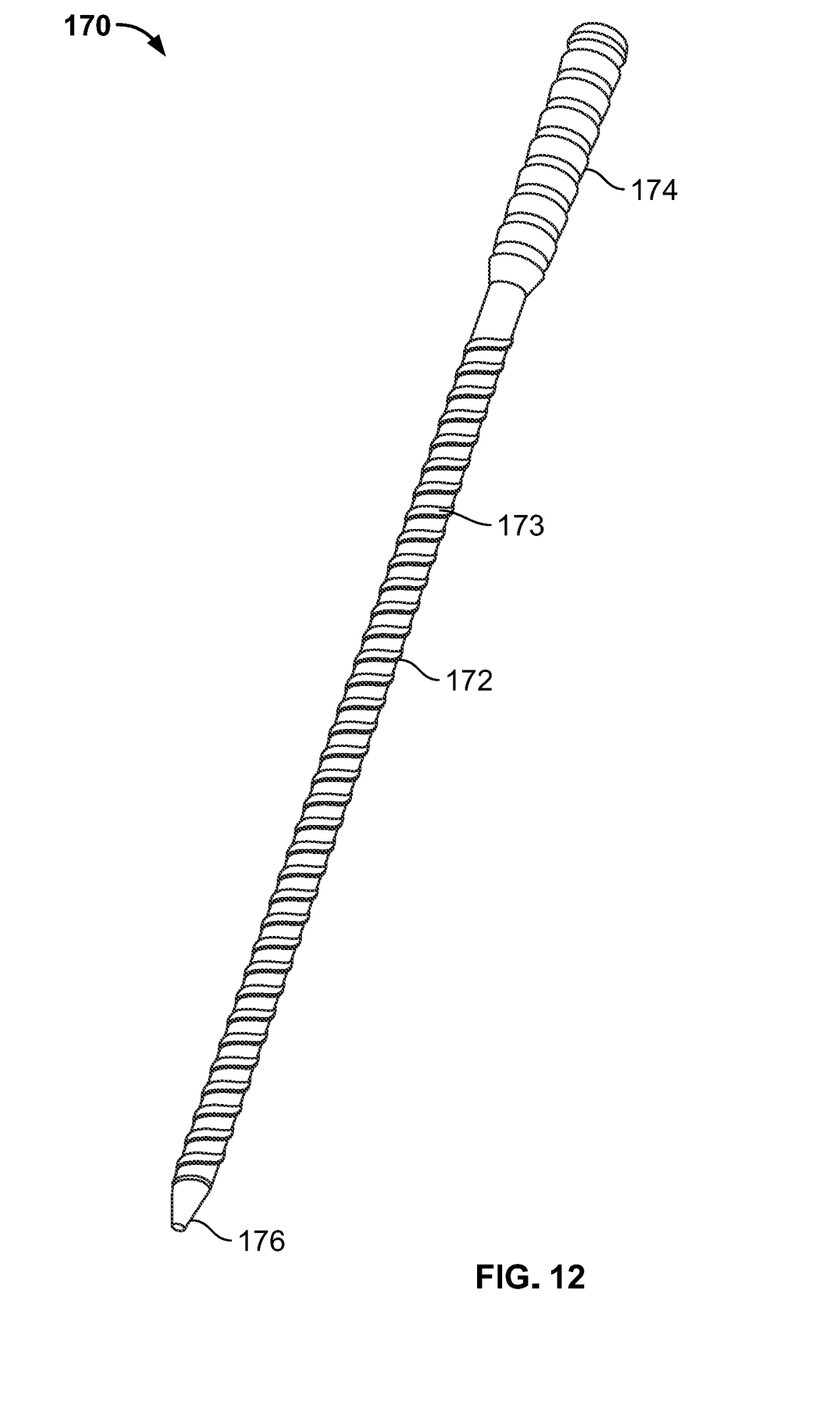
FIG. 12 is a perspective view of a probe according to another embodiment of the disclosure.

FIG. 12 illustrates a probe 170 according to one embodiment of the disclosure. Like reference numerals of probe 170 refer to like elements of probe 10 as illustrated in FIG. 1. Shaft 172 of probe 170 includes a helical groove 173 over a portion of the probe length between handle 174 and tip 176. Probe 170 may be configured with a light emitting device so that upon reaching a threshold nerve stimulation, the device lights up to warn a user that a nerve is close by. In some examples, a light emitting device is attached within the groove of the shaft while in others it is attached to a ridge adjacent to the groove. Probe 170 may be advantageous when a surgical path includes osteophytes or other abnormal anatomy and when it is otherwise difficult to create surgical access with an initial insertion instrument.

Figure 13:
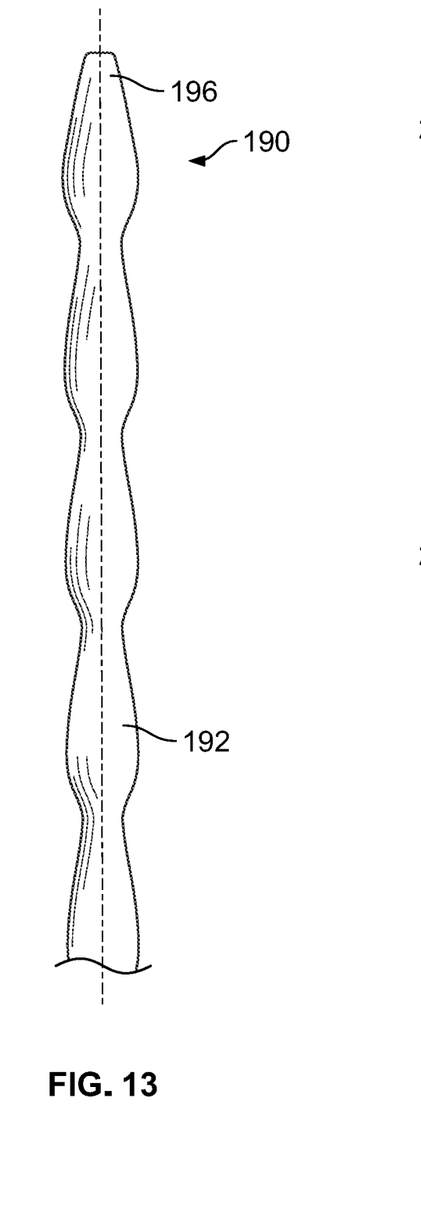
FIG. 13 is a side view of a probe according to another embodiment of the disclosure.
Figure 14:
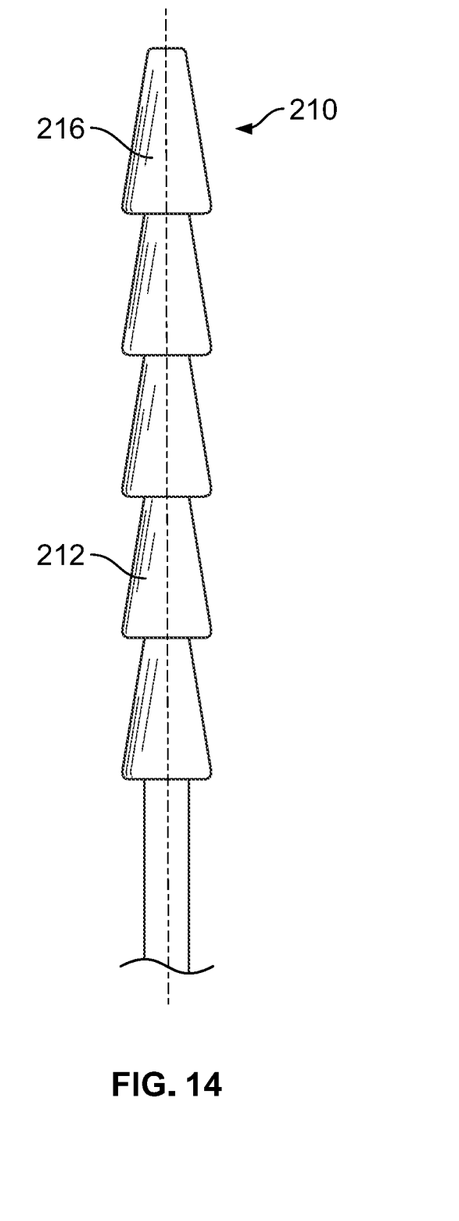
FIG. 14 is a side view of a probe according to another embodiment of the disclosure.

FIGS. 13 and 14 illustrate probes 190, 210 according to respective embodiments of the disclosure. Like reference numerals of probes 190, 210 in FIGS. 13 and 14 refer to like elements of probe 10 as illustrated in FIG. 1. A shaft 192 of probe 190 includes a series of circumferential ridges over its length that repeat in a pattern from a location on the probe to its tip. Probe 210 includes a shaft 212 that also includes a series of circumferential ridges, although the surfaces on shaft 212 are more angular than those of shaft 192.

Figure 15:
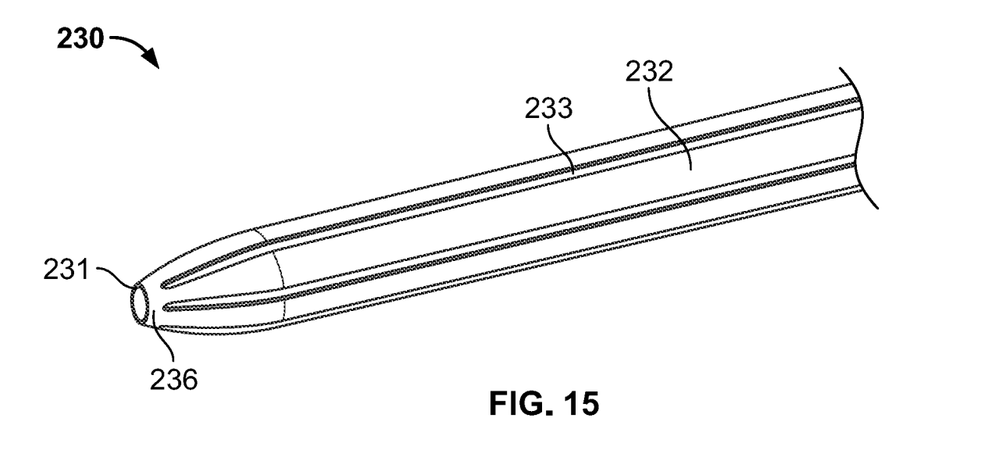
FIG. 15 is a perspective view of a portion of a probe according to another embodiment of the disclosure.
Figure 16:
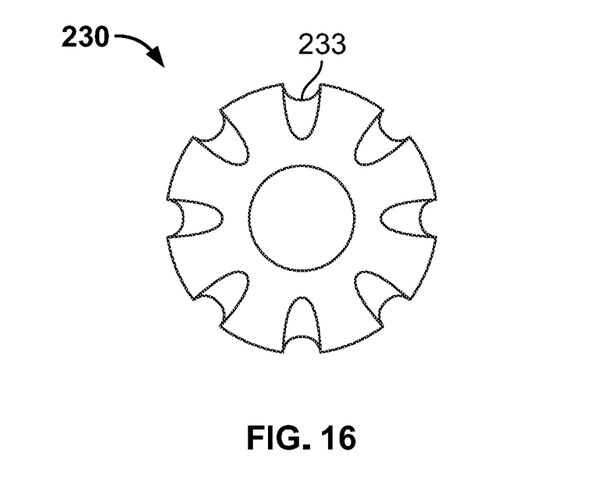
FIG. 16 is a cross-sectional view of the probe of FIG. 15.

FIGS. 15 and 16 illustrate probe 230 according to one embodiment of the disclosure. Like reference numerals of probe 230 in FIGS. 15 and 16 refer to like elements of probe 10 as illustrated in FIG. 1. Probe includes a shaft 232 that extends to a tapering tip 236. On shaft 232 are longitudinally extending grooves 233 spaced around a perimeter of shaft 232. These grooves terminate at a location spaced from terminus 231 of probe 230. The shaft with longitudinally extending grooves is advantageous in that it has a greater surface area than a shaft without such grooves and therefore provides increased grip for the probe. Additionally, the increased grip also functions to provide additional resistance to pull out forces acting on the probe.

Figures 17, 18, 19:
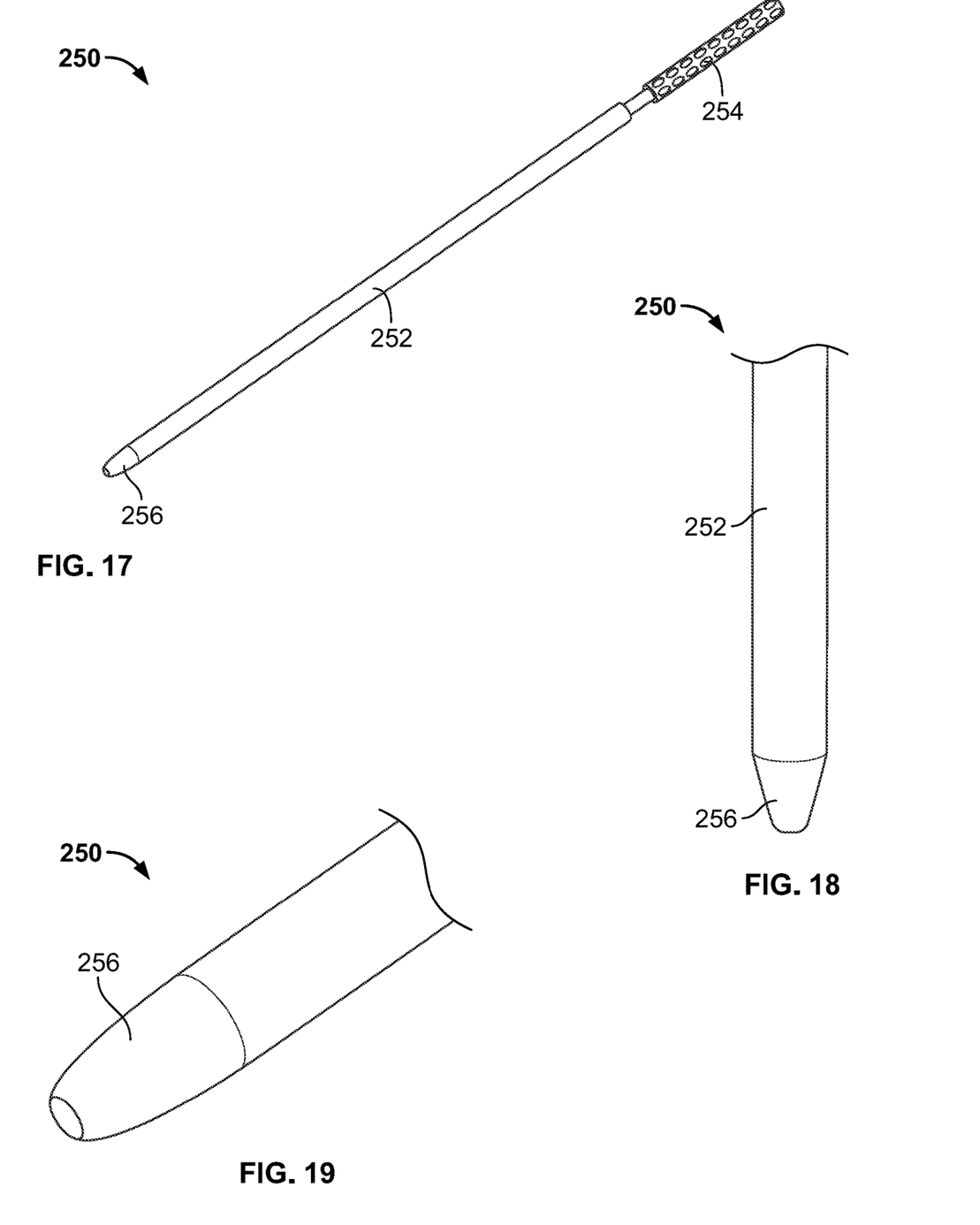
FIGS. 17-19 are views of a probe according to another embodiment of the disclosure.

FIGS. 17-19 illustrate probe 250 according to one embodiment of the disclosure. Like reference numerals of probe 250 in FIGS. 17-19 refer to like elements of probe 10 as illustrated in FIG. 1. Probe 250 includes a rounded tip 256 defined by rounded, smooth surfaces and smooth transition regions.

Figure 20A:
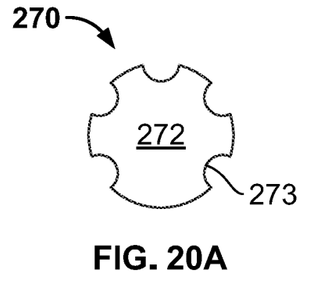
FIGS. 20A and 20B are views of a probe according to another embodiment of the disclosure.
Figure 20B:
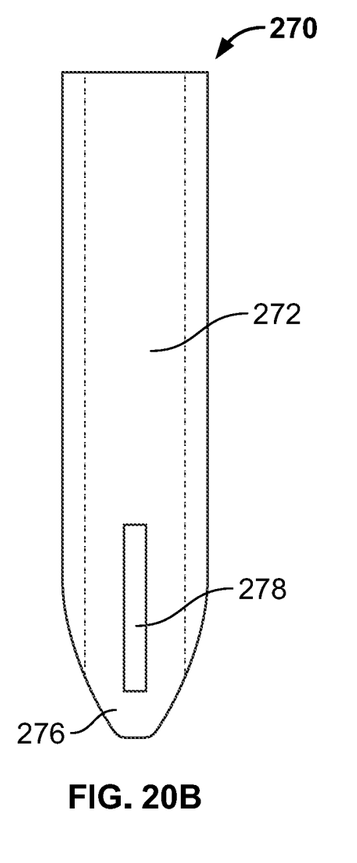
Figure 21A:
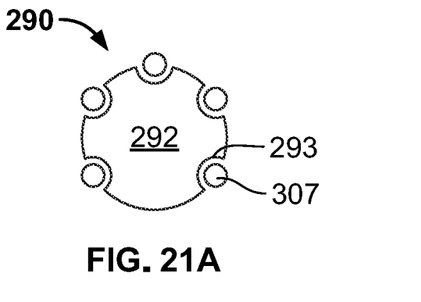
FIGS. 21A and 21B are views of a probe according to another embodiment of the disclosure.
Figure 21B:
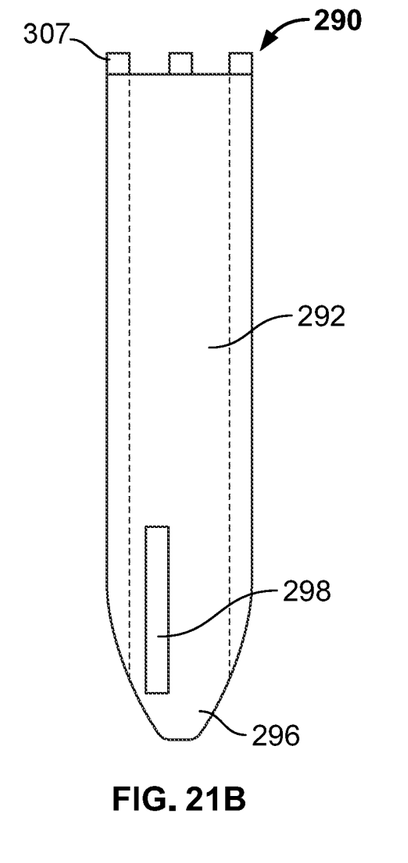

FIGS. 20A-B and 21A-B illustrate views of probe 270 and probe 290 according to respective embodiments of the disclosure. Like reference numerals of probes 270, 290 in FIGS. 20A-B and 21A-B, respectively, refer to like elements of probe 10 as illustrated in FIG. 1. In FIGS. 20A and 20B, probe 270 includes a neuromonitoring element 278 near tip 276 and further includes longitudinally extending grooves 273 spaced around a perimeter of body 272. Probe 270 combines the function of a standard probe with that of an obturator. For example, in a method of use, probe 270 is initially inserted into a wound or other prepared entry point in a body of a patient. During insertion, probe 270 is neuromonitored with element 278. When advancement of the probe is complete, retractor rods are slid over grooves 273 on the probe. If surgery is on the spine, the rods may be docked at this juncture. The probe is then removed and retraction of the retractor may commence. No k-wire is required for this procedure. In another example of a method of use illustrated in FIGS. 21A and 21B, retractor blades 307 are disposed within grooves 293 of probe 290 prior to advancement of the probe into a wound or surgical site. With the rods disposed in respective grooves 293 on probe 290, the rods combined with probe are advanced to the surgical site while being neuromonitored. Once the probe is at a desired position for retraction of the rods, a retractor structure is attached to the rods from above. Then, the probe is removed so that the retractor may be actuated to open a surgical portal.

Figure 22:
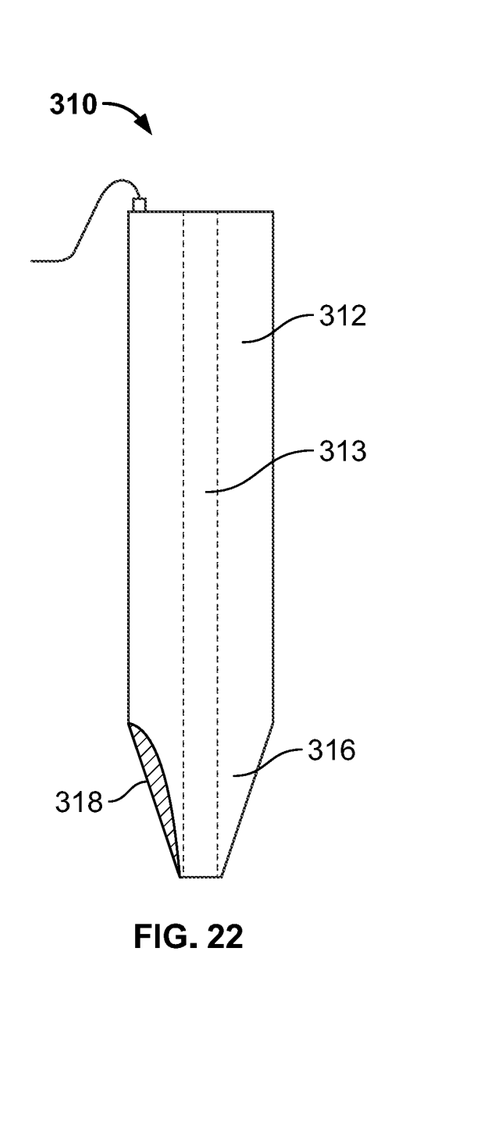
FIG. 22 is a side view of a probe according to another embodiment of the disclosure.

FIG. 22 illustrates probe 310 according to an embodiment of the disclosure. Like reference numerals of probe 310 in FIG. 22 refer to like elements of probe 10 as illustrated in FIG. 1. Probe 310 is made of a clear plastic material, such as acrylic. The probe includes a neuromonitoring conductive zone 318 connected to a neuromonitoring console (not shown). Disposed within body 312 of probe 310 are a series of light emitting devices, such as LEDs (not shown). Light from the light emitting devices is visible through the clear material of the probe, thus providing a visual cue to a user when the devices are on. The light emitting devices provided include lights of at least two different colors. Each device of a particular color is configured to emit light within a unique range of detected electrical activity, e.g., current, that may occur in response to nerve stimulation. In one example, probe 310 includes a blue LED, a yellow LED and a red LED. In operation, while probe 310 is advanced into a body of a patient, neuromonitoring is performed. As the probe is advanced, if a detected current is low, continued advancement of the probe is safe and the blue color LED(s) is signaled to be on while LEDs of all other colors are off. If a detected current is above a safe level but below a dangerous level, then the blue LED(s) turns off and the yellow LED(s) turns on. Similarly, when a detected current is above a dangerous level, the blue LED(s) turns off and the red LED(s) turns on to warn the user that nerves are close.

Figure 23A:
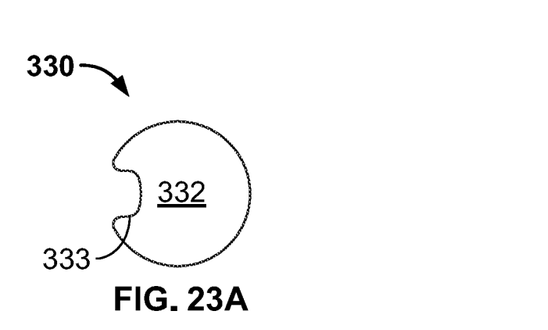
FIGS. 23A and 23B are views of a probe according to another embodiment of the disclosure.
Figure 23B:
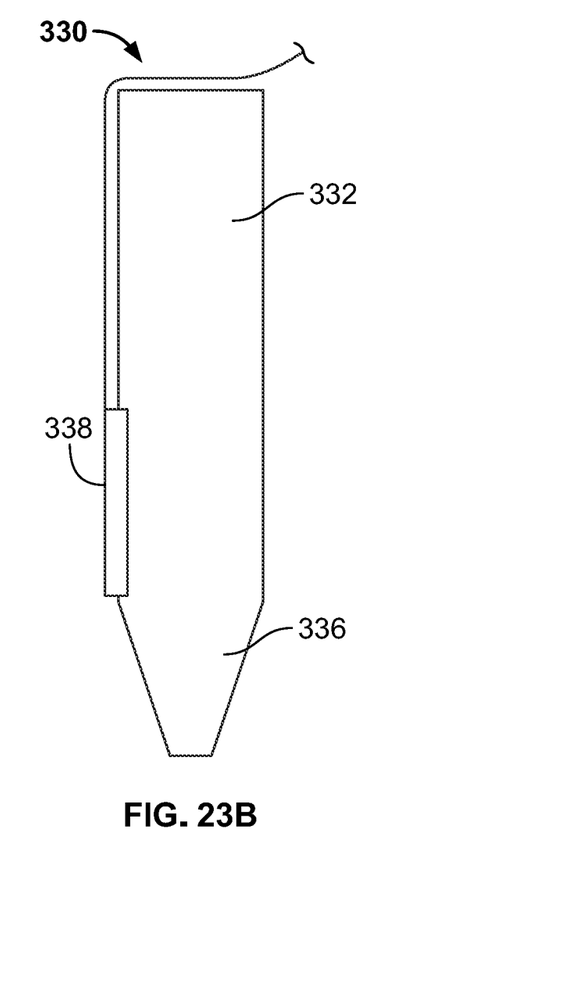

FIGS. 23A-B illustrate a probe according to another embodiment of the disclosure. Like reference numerals of probe 330 in FIGS. 23A-B refer to like elements of probe 10 as illustrated in FIG. 1. Probe 330 is coated with an electrically insulated material and includes a longitudinally extending groove 333 sized to accept a neuromonitoring element 338. A shape of the groove and the neuromonitoring element are complementary so that the neuromonitoring element may snap into place on the probe, as shown in FIG. 23B. In one example, neuromonitoring element 338 is single-use and disposable. A single use neuromonitoring element is advantageous in that it does not degrade or corrode through repeated use.

Figure 24A:
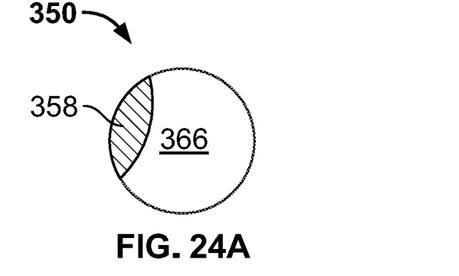
FIGS. 24A and 24B are views of a probe according to another embodiment of the disclosure.
Figure 24B:
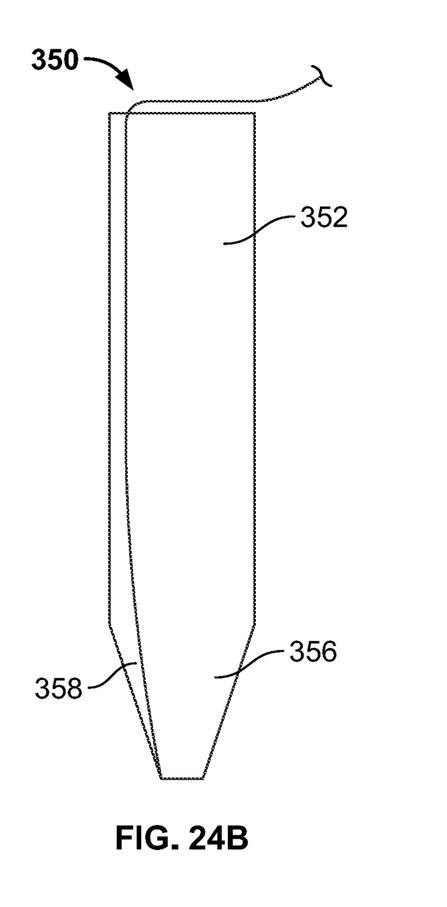

FIGS. 24A-B illustrate a probe 350 according to another embodiment of the disclosure. Like reference numerals of probe 350 in FIGS. 24A-B refer to like elements of probe 10 as illustrated in FIG. 1. As shown in FIG. 24A, a first part 366 of a body 352 of probe 350 is insulated while a second part 358 is conductive and functions as a neuromonitoring element.

Figure 25A:
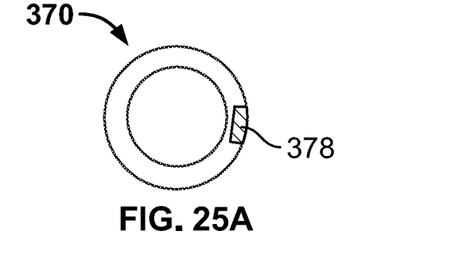
FIGS. 25A and 25B are views of a probe according to another embodiment of the disclosure.
Figure 25B:
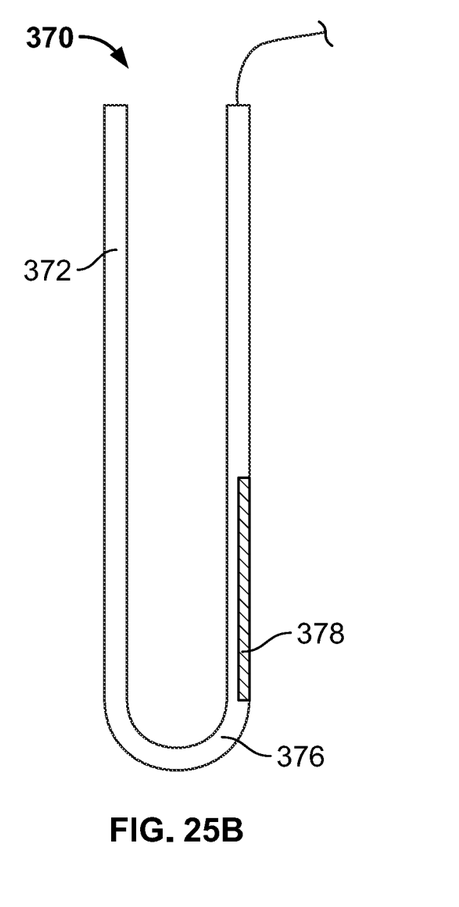

FIGS. 25A-B illustrate a probe 370 according to another embodiment of the disclosure. Like reference numerals of probe 370 in FIGS. 25A-B refer to like elements of probe as illustrated in FIG. 1. Probe 370 is a tube 372 with a neuromonitoring element 378 on its external surface. Tube 372 is made of a plastic material. In use, probe 370 is slid over a rod of a retractor.

Figure 26:
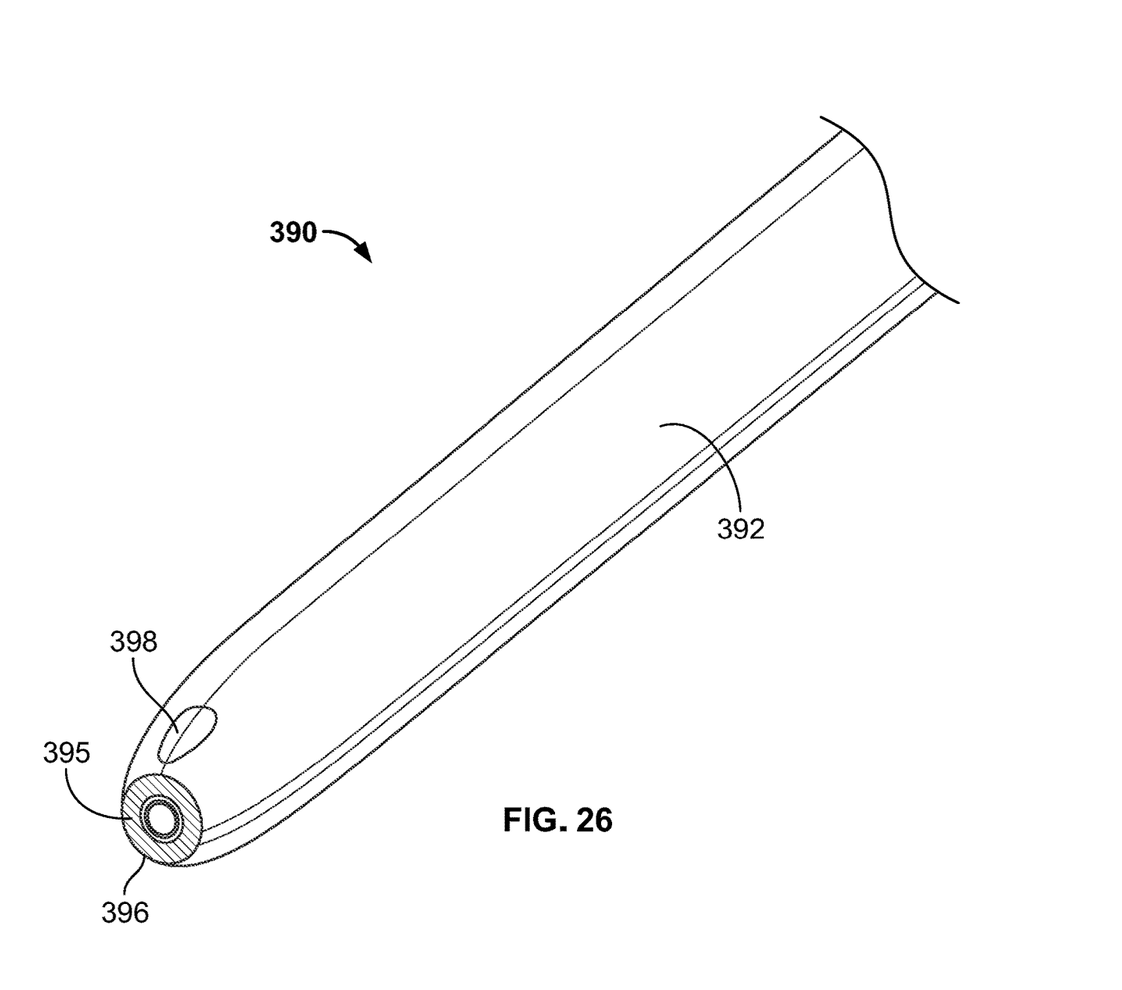
FIG. 26 is a perspective view of a probe according to another embodiment of the disclosure.

FIG. 26 illustrates a probe 390 according to another embodiment of the disclosure. For probe 390, unless otherwise noted, like reference numerals refer to like elements of probe 10, but within the 390 series of numbers. Probe 390 includes a shaft 392 extending to a tip 396. The shaft tapers toward tip 396 as shown in FIG. 26. Adjacent to the tip is a neuromonitoring element 398. On an end surface at the tip is an ultrasound sensor 395. The ultrasound sensor, when operative, detects a proximity of objects from the sensor on the probe. Thus, for example, when the probe is advanced into a patient, the ultrasound sensor may detect the proximity of bone, tissue, intervertebral discs, or other internal organs. The ultrasound sensor may also be used as a Doppler probe, either separately or simultaneously with its use as an ultrasound sensor. As a Doppler probe, a surgeon may listen for different sounds as an indication of a proximity of anatomy. It should be appreciated that the ultrasound sensor may be employed in other embodiments of the probe as described herein, including, for example, probes 10, 30, 50, 70, 90, 110, 130, 150, 170, 190, 210, 230, 250, 270, 290, 310, 330, 350, 370.

In any one of the above embodiments, the probe may be cannulated. Moreover, shapes and materials for the probe may vary in any one of the above embodiments to suit desired applications and surgeon preference. Further, in any one of the above embodiments, one or more light emitting devices may be attached or otherwise included on a surface of a probe. Further, in any embodiment that includes neuromonitoring, a wire connection may be provided to a neuromonitoring console.

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

The invention claimed is:

1. A probe for minimally invasive surgery comprising:
a body having a length including a shaft portion and a tapered convex tip portion, the body including a plurality of circumferential ridges spaced apart from one another along the shaft portion so as to define a path for advancement of a retractor rod through said ridges,
a connector electrically connected with a conductive part of the tapered convex tip, the connector capable of being connected to an external source of electricity so that the conductive part delivers electrical stimulation when the conductive part receives electric current; and
a first light emitting device adapted to emit a first color when a first range of electrical activity is detected by the probe and a second light emitting device adapted to emit a second color when a second range of electrical activity is detected by the probe, the first color being different from the second color and the first range being different from the second range.

2. The probe of claim 1, wherein the plurality of circumferential ridges extend over the length of the body from a first end of the body to a second end of the body opposite the first end.

3. The probe of claim 1, wherein the body is a tube with a hollow interior and a closed tip.

4. The probe of claim 1, wherein each of the plurality of circumferential ridges are frusto-conical in shape.

5. A surgical probe comprising:
a shaft having a tapered convex tip including a conductive portion,
a plurality of circumferential ridges spaced apart from one another defined along the shaft that define a path for advancement of a retractor rod, a connector arranged in electrical communication between the conductive portion and a source of electrical activity so that the conductive part provides electrical stimulation; and
a first light emitting device adapted to emit a first color when a first range of electrical activity is detected by the probe and a second light emitting device adapted to emit a second color when a second range of electrical activity is detected by the probe, the first color being different from the second color and the first range being different from the second range.

6. The probe of claim 5, wherein the plurality of circumferential ridges extend over the length of a hollow shaft from a first end to a closed second end.

7. The probe of claim 5, wherein each of the plurality of circumferential ridges are frusto-conical in shape.

* * * * *